US006245200B1

(12) United States Patent
Wilcoxon

(10) Patent No.: US 6,245,200 B1
(45) Date of Patent: Jun. 12, 2001

(54) PHOTO-OXIDATION METHOD USING $MOS_2$ NANOCLUSTER MATERIALS

(75) Inventor: Jess P. Wilcoxon, Albuquerque, NM (US)

(73) Assignee: Sandia Corporation, Albuquerque, NM (US)

(*) Notice: Subject to any disclaimer, the term of this patent is extended or adjusted under 35 U.S.C. 154(b) by 0 days.

(21) Appl. No.: 09/459,059

(22) Filed: Dec. 10, 1999

(51) Int. Cl.[7] .............................. C07C 1/00; C07C 17/00
(52) U.S. Cl. ................................ 204/157.15; 204/157.95; 204/157.97; 204/157.98; 204/157.99
(58) Field of Search ......................... 204/157.15, 157.95, 204/157.97, 157.98, 157.99

(56) References Cited

U.S. PATENT DOCUMENTS 5,147,841 9/1992 Wilcoxon ............................. 502/173

FOREIGN PATENT DOCUMENTS 00-41667 * 2/2000 (JP) .

OTHER PUBLICATIONS

Thurston et al., "Photooxidation of Organic Chemicals Catalyzed by Nanoscale MoS2", J. Phys. Chem. B, (no month available) 1999, pp. 11–17.*

Wilxocon et al., "Synthesis and Optical Properties of MoS2 and Isomorphous Nanoclusters in the Quantum Confinement Regime", J. Appl. Phys., vol. 81, No. 12, Jun. 15, 1997, pp. 7934–7944.*

Serpone, N., "A decade of heterogeneous photocatalysis in our laboratory: pure and applied studies in energy production and environmental detoxification," Res. Chem. Intermed., 1994, 20, 9, 953–992. No month available.

Thurston, T. and Wilcoxon, J., "Photooxidation of organic chemical catalysed by nanoscale $MoS_2$, " J. Phys. Chem. B, 1999, 103, 11–17. No month available.

Wilcoxon, J., Newcomer, P., and Samara, G., "Synthesis and optical properties of $MoS_2$ and isomorphous nanoclusters in the quantum confinement regime," J. Appl. Phys., 1997, 81, 12, 7934–7944. No month available.

* cited by examiner

*Primary Examiner*—Edna Wong
(74) *Attorney, Agent, or Firm*—Elmer A. Klavetter

(57) ABSTRACT

A method of photo-oxidizing a hydrocarbon compound is provided by dispersing $MoS_2$ nanoclusters in a solvent containing a hydrocarbon compound contaminant to form a stable solution mixture and irradiating the mixture to photo-oxide the hydrocarbon compound. Hydrocarbon compounds of interest include aromatic hydrocarbon and chlorinated hydrocarbons. $MoS_2$ nanoclusters with an average diameter less than approximately 10 nanometers are shown to be effective in decomposing potentially toxic aromatic and chlorinated hydrocarbons, such as phenol, pentachlorophenol, chlorinated biphenols, and chloroform, into relatively non-toxic compounds. The irradiation can occur by exposing the $MoS_2$ nanoclusters and hydrocarbon compound mixture with visible light. The $MoS_2$ nanoclusters can be introduced to the toxic hydrocarbons as either a $MoS_2$ solution or deposited on a support material.

13 Claims, 4 Drawing Sheets

PHOTO-OXIDATION METHOD USING $MOS_2$ NANOCLUSTER MATERIALS

This invention was made with Government support under Contract No. DE-AC04-94AL85000 awarded by the Department of Energy. The Government has certain rights in the invention.

BACKGROUND OF THE INVENTION

The invention describes a method for using nanosized semiconductor materials to decompose toxic organic materials and more particularly, to a method of using $MoS_2$ nanosized particles to decompose aromatic and halogenated hydrocarbons by photo-oxidation.

Contamination of sediments and aqueous water systems by halogenated organic compounds presents a serious environmental threat due to their toxicity and resistance to biodegradation. These chemicals are widely employed as pesticides, insecticides, and wood preservatives and thus are ubiquitous in the environment of both industrialized and agrarian nations. Even chemicals that have been banned for years, like dichlorodiphenyltrichloroethane (DDT) and its analogues, still pose major environmental threats. A subgroup of these toxic chemicals, referred to as chlorinated aromatics, includes chlorinated benzenes and biphenyls (PCBs), pentachlorophenol (PCP) and insecticides such as DDT.

In general, the more halogenated atoms, such as chlorine, on the aromatic phenol ring, the greater the biohazard. The widespread proliferation of PCP and its analogues in the environment can also result from combustion, water treatment with chlorine in the presence of organic materials, and municipal sewage treatment plants and incinerators. Once discharged into the environment, these water insoluble compounds seep into the sediment of rivers, lakes, and other bodies of water and continually leach out into the water supply, potentially affecting the entire mammalian food chain.

Microbial degradation and naturally occurring hydrolysis of these compounds is a very slow process (for example, for 4-cholorophenol at 9° C., the half life is nearly 500 days). Some direct photo-degradation also occurs, though the limited absorbance of chlorinated aromatics above 350 nm makes this process painfully slow. Sometimes this direct photolysis can actually lead to more toxic products. Direct photolysis of PCP has been reported to lead to octachlorodibenzo-p-dioxin, an even more toxic species than its precursor.

Effective methods of treatment of these chlorinated aromatics are being sought. Photocatalytic oxidation of these compounds to form harmless $CO_2$ and HCI, a process referred to as total mineralization has been investigated. The semiconductor catalyst of choice in these studies has generally been $TiO_2$, a white, photostable, non-toxic powder, whose principal deficiency is an absorbance edge which starts at about 385 nm, allowing less than 3% utilization of the solar spectrum. Serpone (Serpone, N., Res. Chem. Intermed., 1994, 20, 9, 953–992) provides a description of the use of $TiO_2$ in heterogeneous photocatalysis to detoxify various organic materials. Serpone observes that $TiO_2$ absorbs only about 3% of solar radiation and thus is not very efficient in using natural light to decompose toxic organic compounds.

It would be useful to have a visible-light-absorbing semiconductor catalytic material available that is photostable and non-toxic and that can utilize visible light to decompose toxic organic materials. Thurston and Wilcoxon (Thurston, T. and Wilcoxon, J., The J. of Physical Chemistry, 1999, 103, 1, 11–17; incorporated by reference herein) demonstrate the use of new $MOS_2$ photocatalysts to destroy phenol, and demonstrated a strong effect of size or band-gap on the rate of photo-oxidation.

SUMMARY OF THE INVENTION

According to the present invention, a method of photo-oxidizing a hydrocarbon compound is provided by dispersing $MoS_2$ nanoclusters in a solvent containing a hydrocarbon compound contaminant to form a stable solution mixture and irradiating the mixture to photo-oxide the hydrocarbon compound. Hydrocarbon compounds of interest include aromatic hydrocarbon and chlorinated hydrocarbons. $MOS_2$ nanoclusters with an average diameter less than approximately 10 nanometers are more effective than larger-size $MOS_2$ nanocluster materials. The irradiation can occur by exposing the $MOS_2$ nanoclusters and hydrocarbon compound mixture with visible light. Hydrocarbon compounds that are of concern to be photo-oxidized by the method of the present invention include phenol, pentachlorophenol, chlorinated biphenols, and chloroform.

In one embodiment, the $MoS_2$ nanoclusters are added as a solution directly to the solution containing the hydrocarbon compounds to be photo-oxidized. In another embodiment, the $MoS_2$ nanoclusters are deposited on a support material before contacting the hydrocarbon compounds.

In another embodiment, the present invention provides a method of enhancing the photocatalytic activity of photocatalysts selected from the group consisting of $TiO_2$, $SnO_2$, and $MoS_2$ nanoclusters by adding less than approximately 1 wt % of a water soluble, micelle-forming, photostable cationic surfactant.

DESCRIPTION OF SPECIFIC EMBODIMENTS

Figure 1:
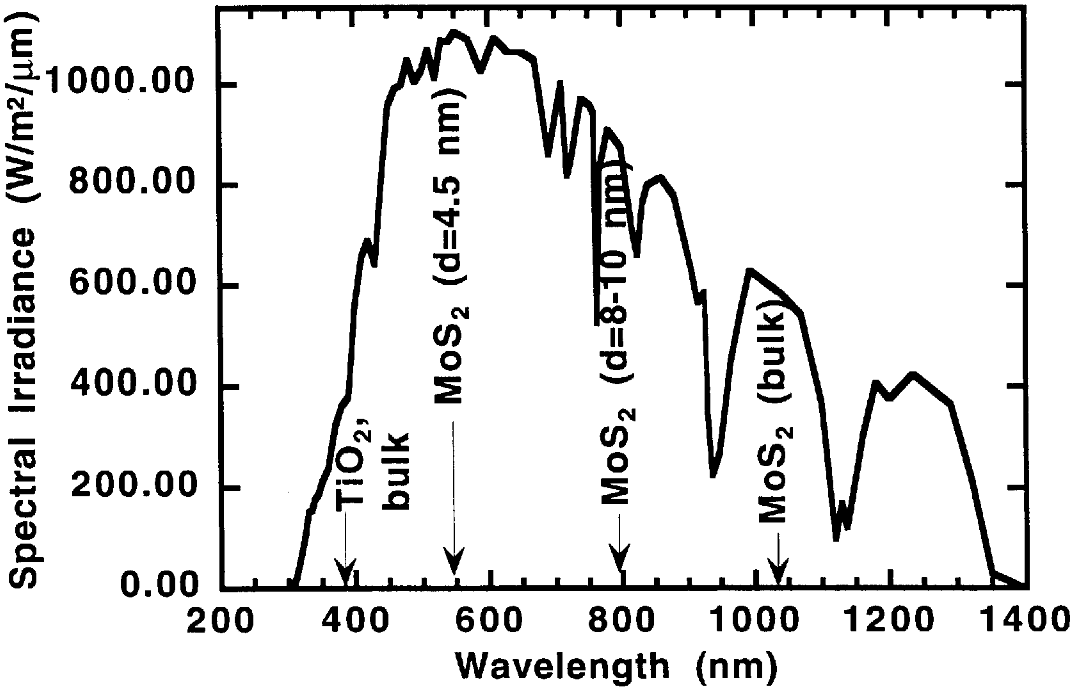
FIG. 1 shows the spectral irradiance of the solar radiation reaching the earth's surface as a function of photon wavelength.

The electron-hole pairs generated by solar radiation in semi conducting materials can catalyze reduction-oxidation (redox) reactions that can destroy organic chemicals, such as aromatic and halogenated hydrocarbons. One difficulty with many potential catalytic compounds is that the compounds absorb only a small fraction of the solar spectrum. FIG. 1 shows the spectral irradiance of the solar radiation that reaches the earth's surface as a function of photon wavelength. Only photons with wavelengths smaller than the band gap wavelength can excite electron-hole pairs. For bulk $TiO_2$, this wavelength is in the near-ultraviolet (UV) region or about 390 nm. This means that, for bulk $TiO_2$, only about 3% of the solar spectrum is utilized.

Wilcoxon (wilcoxon, J.P., U.S. Pat. No. 5,147,841, issued Sep. 15, 1992; incorporated herein by reference) and Wilcoxon et al. (Wilcoxon, J., Newcomer, P, and Samara, G., J. Appl. Phys., 1997, 81,12, 7934-7944; incorporated herein by reference) demonstrated that nanoclusters of $MoS_2$ could be prepared using an inverse micelle synthesis process. The absorbance wavelength of these nanoclusters of $MoS_2$ can be varied by varying the size of the nanocluster materials. FIG. 1 shows that for $MoS_2$ particles with an average diameter of 4.5 nm, the absorbance onset is approximately 550 nm and, for particles with an average diameter of 8–10 nm, the absorbance edge is approximately 800 nm. These particles can thus potentially utilize a much greater fraction of solar radiation.

Figure 2:
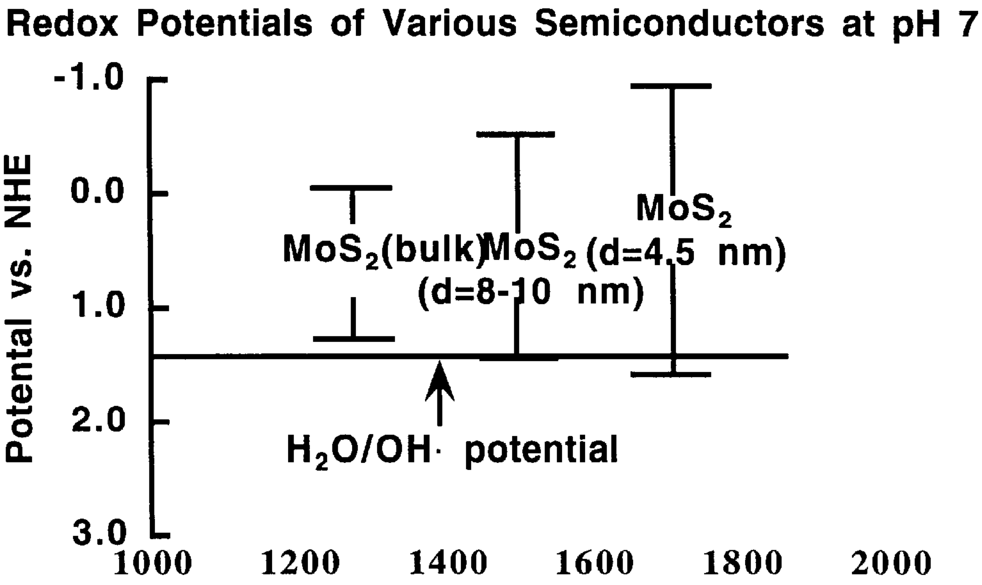
FIG. 2 shows the reduction-oxidation (redox) potential for $MoS_2$ materials.

For the toxic organic compounds to be photo-oxidized, a catalyst must be introduced which can produce hole-electron pairs and thus hydroxyl radicals from water. These hydroxyl radicals are created due to the absorbance of visible light which creates hole-electron pairs. The hole oxidizes the water to form surface adsorbed hydroxyl radicals which can attack the organic pollutant. The holes themselves also can directly attack adsorbed organic molecules. The electron can be transferred to any oxygen present to form a powerful dioxygen free-radical oxidant which also readily attacks organic molecules. FIG. 2 shows the redox potentials of various $MoS_2$ materials. For a pH=7 solution, the production of hydroxyl radicals occurs when the semiconductor valence band potential is larger than approximately +1.2–1.5 V. FIG. 2 shows that bulk $MoS_2$ does not have an oxidation potential sufficiently large to produce hydroxyl radicals. However, nanoclusters of $MOS_2$ do possess sufficiently large oxidation potentials.

According to the method of the present invention, surfactant stabilized $MoS_2$ nanocluster powders are mixed into a solvent, such as water or any inert polar organic, for example acetonitrile (ACN), in the presence of aromatic or chlorinated hydrocarbons at near saturation values (for example, 10–100 ppm). This mimics the situation in the environment where dense non-aqueous sediments and soils continually leach out toxic pollutants into the water table. The typical photocatalyst concentrations used in this work are much less than required with conventional $TiO_2$ photocatalysts (for example, approximately 0.1 mg/ml of MoS2 nanoclusters are used compared to 1.0–2.0 mg/ml used in previous work using $TiO_2$). The resulting non-scattering but strongly light absorbing solution is exposed to light such as solar radiation. A Xe arc lamp with appropriate filters to cut-off all UV and IR radiation can be used to mimic the solar spectrum. The $MoS_2$ acts as a semiconductor catalyst to form hole-electron pairs which in turn oxidize the toxic hydrocarbon compounds into less toxic decomposition products. In particular, we have demonstrated that complete mineralization of the organics pentachorophenol (PCP), 4-Cl phenol, and phenol into $C\mathbf{0}_2$ and HCI. HPLC has been used to demonstrate complete destruction of the organic to less than 20 ppb levels while also showing the MoS2 to be photostable and reusable with no loss in activity.

The $MoS_2$ nanocluster materials can be synthesized by the method described by Wilcoxon et al. (1997). A Mo(lV) halide, such as $MoCI_4$ is dispersed in a water-free and air-free inverse micelle system consisting of a nonionic or cationic surfactant in a nonpolar solvent, such as an oil such as toluene or an alkane such as octane, containing a cosurfactant. The surfactant can include any surfactant soluble in the nonpolar solvent, such as didodecyidimethylammonium bromide (DDAB) and didodecyldimethylammonium chloride (DDAC). The cosurfactant includes such compounds as alcohols, such as pentanol, hexanol and heptanol. The solution is reacted under inert atmosphere with a stoichiometric excess of sulfiding agent such as $H_2S$ (gas) or $(NH_4)_2S$ (liquid) to form $MOS_2$ nanocrystals. Another cationic surfactant, such as DDAB or DDAC, soluble in water or polar organics such as ACN, methanol, (MeOH) or tetrahydrofuran (THF) is then added to ACN and the nanoclusters are extracted from the non-polar oil phase into the polar ACN phase, dried, and then redispersed into water for use as a photocatalyst. The dispersed nanosize photocatalysts may be further purified by dialysis if desired using a low molecular weight cut-off dialysis membrane. However, this last step is not necessary to obtain high catalytic activity. The size of the nanoclusters formed is determined by the strength of binding of the surfactant to the surface during the growth process and its concentration during the growth process, with smaller concentrations or weaker binding producing large nanoclusters. All nanocluster catalyst solutions as prepared showed negligible light scattering. The $MoS_2$ particles are generally very monodisperse as confirmed by HPLC size distribution analysis with the size controlled by selection of surfactant and surfactant concentration.

Using the surfactant tridodecylmethylammonium chloride (TDAC) at a concentration of approximately 8%, hexanol at 10%, and the remainder octane, $MOS_2$ particles are formed with an average diameter, as determined by lightscattering and high-resolution transmission electron microscopy (HRTEM), of approximately 3.0 nm. In a solution using the surfactant didodecyldimethylammonium bromide (DDAB) at a concentration of approximately 10%, hexanol at 11%, and the remainder decane, $MoS_2$ particles are formed with an average diameter, as determined by light-scattering and transmission electron microscopy techniques, of approximately 4.5 nm. In a solution using the surfactant DDAB in toluene at a concentration of approximately 0.5%, $MoS_2$ particles are formed with an average diameter, as determined by light-scattering and TEM, of approximately 8–10 nm. The as-synthesized $MOS_2$ clusters were purified to remove excess reactants, surfactants or reaction by-products by extraction from octane into acetonitrile, dried, and then added to water to form the catalyst solution as noted above.

Figure 3:
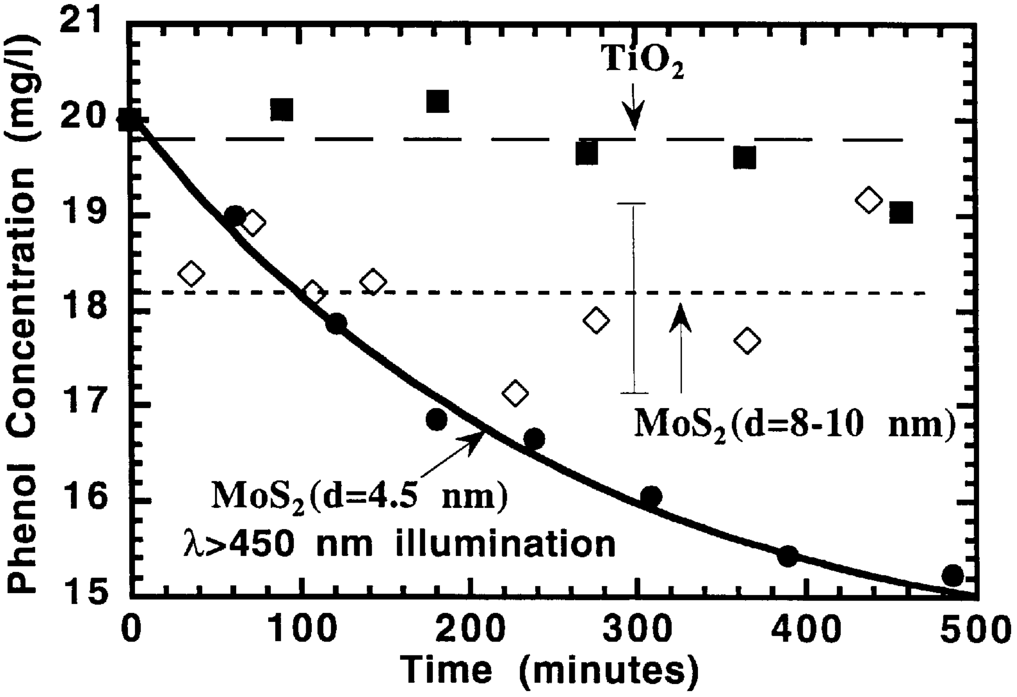
FIG. 3 shows phenol photo-oxidation.

In one embodiment demonstrating the capability to photo-oxidize toxic organic chemicals, these solutions were exposed to chemicals including pentachlorophenol (PCP), 4-Cl phenol and phenol. $MoS_2$ nanoclusters of average diameter 4.5 nm and of average diameter 8–10 nm and a concentration of 0.09 mg/ml were added to 20 mg/L phenol solution and exposed to visible light. While a control sample of $TiO_2$ showed little oxidation of the phenol, the $MOS_2$ (diameter=8–10 nm) resulted in approximately 10–15 percent reduction in phenol concentration within a few hours and $MoS_2$ (diameter=4.5 nm) resulted in approximately 25 percent reduction in phenol concentration within approximately eight hours, as shown in FIG. 3. Within 24 hrs, all of the measurable phenol was destroyed with the smaller d=4.5 nm clusters. Control experiments demonstrated that the decrease in phenol concentration was due to the $MoS_2$ catalyst when exposed to radiation of greater than 450 nm in wavelength. Control experiments using the best commercial $TiO_2$ photocatalyst, at 1 mg/ml showed no activity under these conditions.

The $MoS_2$ nanoclusters were shown to be stable against agglomeration in water when the average particle size was approximately 8–10 nm. The $MoS_2$ nanoclusters of average particle size of approximately 4.5 nm and 3.0 nm were shown to be stable against agglomeration in water when capped by a surfactant or when a coordinating solvent like ACN or THF was introduced into the water. The water-soluble, cationic surfactant stabilizers used, DTAC and DTAB, were found to actually lead to an increase in the photocatalytic oxidation activity in the range of when tested at concentrations of less than approximately 1% while suffering no photodegradation themselves. This enhancement effect could be due to better solubilization of the water insoluble chlorinated aromatic organics by the surfactant micelles.

In another embodiment, the $MoS_2$ catalytic nanocluster materials were deposited on a support material. Catalytic materials are often deposited on a powder support material, particularly when used in many reactor configurations. $MoS_2$ catalytic nanocluster materials were deposited onto $TiO_2$, $SnO_2$, $WO_3$, and ZnO by mixing the powdered support material into a solution of $MoS_2$ nanoclusters and then dried, such as by heating or centrifugation under a vacuum, to remove the solution. Under visible illumination (where $TiO_2$ and the other metal oxide powders are non-absorbing and thus completely inactive) only the supported $MoS_2$ nanoclusters on $TiO_2$ showed activity for photo-oxidation of aromatic hydrocarbons. The principal demonstrated is the ability to collect light by a photostable inorganic material, $MoS_2$ and transfer the hole to the more positive valance band of $TiO_2$, leading to improved charge separation and hence carrier lifetime. This extended carrier lifetime increases the probability of oxidation of the organic or creating of surface bound hydroxyl radicals by the hole, and thus improves the catalytic activity.

Other materials beside $MoS_2$ were investigated to determine if they could be used to effectively photo-oxidize toxic hydrocarbon compounds. It has been previously demonstrated that $RuO_2$ and $PtS_2$ deposited on colloidal $TiO_2$, when prepared as semi-conductor photoelectrodes, are effective photo-electro-oxidation catalysts. Tests were performed to determine if bulk powders of these materials would provide good photo-oxidation of organics like PCP. The results were surprising, showing that these materials actually reduced the rate of normal photolysis, preserving the PCP. This result was also found to be true of bulk powders of $MoS_2$, $WO_3$, and $SnO_2$. This effect emphasizes the remarkably rapid rates of photo-oxidation observed in nanosize $MoS_2$ semiconductors, especially since $PtS_2$ has the same layered hexagonal structure found in $MoS_2$.

EXAMPLES

Example 1.

Photo-oxidation of Phenol

The photo-oxidation tests were performed in a photo-oxidation reactor consisting of a cylindrical reactor with a flat glass base and an o-ring sealed quartz, threaded window holder, with an aperture (approximately 3 cm) larger than the collimated Xe lamp output beam (approximately 1.5 cm). The reactor has a total volume of about 60 ml; the tests used about 40 ml of liquid in all reactions. A 0.6 ml aliquot of the sample was removed at various irradiation times for analysis. This aliquot was filtered using an HPLC filter (0.45 micron, cellulose) to remove any suspended catalysts into a standard 2 ml crimp-top HPLC vial for either HPLC or GC/MS analysis. Standards of 10, 1 and 0.1 ppm of phenol and H20 were used to quantify the HPLC peak elution area results and determine that all organics were removed from the water by the photocatalyst. A commercial 400 Waft Xe-arc lamp was used as the irradiation source as the output of this lamp is very close to that of the solar spectrum when combined with the 700 nm short-pass filter used. To study only visible light photo-oxidation, a 400 nm long-pass filter was also used to limit the incident irradiation wavelengths, 400 nm<λ<700 nm. The lamp light output is monitored continuously by a power meter with a computer to track total irradiation time and any power variations. The incident power was measured using a 1-$cm^2$ size calibrated photodiode probe. Neutral density filters on quartz substrates were used to attenuate the incident light by known amounts.

Solutions containing $MoS_2$ nanoclusters were exposed to phenol. $MoS_2$ nanoclusters of average diameter 4.5 nm and of average diameter 8–10 nm and a concentration of 0.09 mg/ml were added to 20 mg/L phenol solution and exposed to visible light. While a control sample of $TiO_2$ showed little oxidation of the phenol, the $MoS_2$ (diameter of 8–10 nm) resulted in approximately 10–15 percent reduction in phenol concentration within a few hours and $MoS_2$ (diameter of 4.5 nm) resulted in approximately 25 percent reduction in phenol concentration within approximately eight hours, as shown in FIG. 3. Within 24 hrs, all of the measurable phenol was destroyed with the smaller diameter of 4.5 nm clusters.

Example 2.

Photo-oxidation of Pentachlorophenol, PCP

Figure 4:
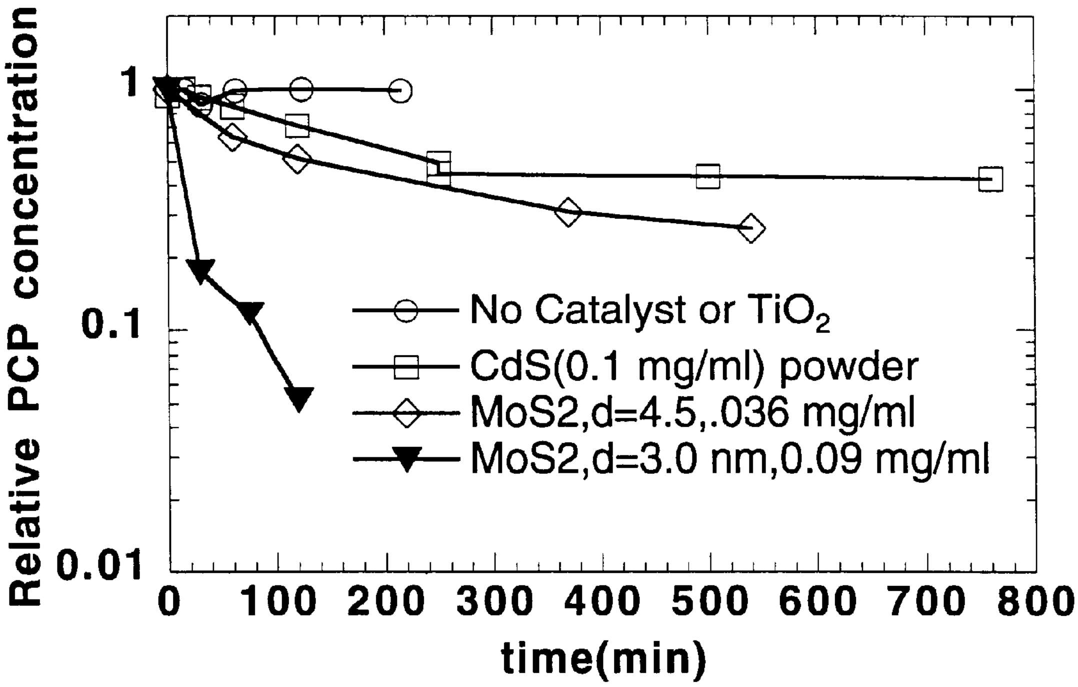
FIG. 4 shows pentachlorophenol photo-oxidation.

To study the rate of photo-oxidation of PCP, a High Pressure Liquid Chromatography (HPLC) system equipped with a photodiode array, (PDA), a refractive index, (RI), and a fluorescence, (FL), detector was used. $MoS_2$ nanoclusters were prepared with an average diameter of approximately 3 nm and 4.5 nm using the inverse micelle preparation method described previously. The 3-nm particles were at a concentration of 0.09 mg/ml. The 4.5-nm particles were at a concentration of 0.036 mg/ml. The results are shown in FIG. 4 which demonstrate the PCP photo-oxidation as a function of time. At the conclusion of several of the reactions that were run long enough to achieve greater than 99% disappearance of the PCP, verification using a potentiometric Cl selective electrode was obtained that the expected amount of free chloride was generated as calculated from the initial concentration of 10 ppm PCP. This demonstrates that complete detoxification was accomplished with the $MoS_2$ nanosize photocatalysts using only visible illumination. By comparison, a strongly visibly absorbing commercial powder of CdS at 10 times the concentration of the $MoS_2$ nanoclusters showed much less activity. Note also in FIG. 4 the strong nanocluster size-effect on the rate of photo-oxidation, which we attribute to the alteration of the electronic conduction and valance band energies of the nanocrystal to more favorable levels as the clusters become smaller. This effect can be exploited to enhance the activity in the addition to the obviously larger surface area/gram of the smaller clusters. This principal should be general to a wide range of semiconductor materials; however, only photostable covalent semiconductors like $MoS_2$ or $WS_2$ will be kinetically stable against lattice photo-oxidation, and thus useful as photocatalysts. The shifting of the energy levels is predicted by quantum confinement of the electron-hole pair created by absorbtion of a visible photon and is the first demonstrate the usefulness of this effect in a practical photo-oxidation experiment.

Example 3.

Effect of Surfactants, Multiple Organic Pollutants, and Salts on PCP Photo-oxidation Because in many real world situations, there are both multiple organic pollutants, inorganic salts, and even surfactants present in the water, tests were performed to determine separately the effect of a simple, common salt, NaCI, and a common type of organic, water soluble surfactant, a quaternary ammonium salt, dodecyltrimethylammonium chloride (DTAC) on the photo-oxidation kinetics. These tests showed that even low levels of NaCI have a poisoning effect on standard photo catalysts like $TiO_2$. Similar observations have been made in field tests of $TiO_2$ where de-ionization of the aqueous Waste stream has been found to be necessary. $MoS_2$ nanoclusters in fully dispersed form are much less sensitive to the solution ionic strength and pH, a further advantage of these new nanosize materials. Of even more significance is the acceleration of the photo-oxidation of PCP in the presence of the DTAC surfactant. Similar observations were made of acceleration of the photo-oxidation kinetics for nanosize $MoS_2$. The use of a similar surfactant, dodecyltrimethylammonium bromide, DTAB also, accelerates the photo-oxidation, though not as much as DTAC, and these increases in photo-oxidation rate are also seen using ACN as a solvent. At the same time, the HPLC elution peak corresponding to DTAC doesn't change in position or area, showing that these surfactants are robust compared to PCP during photo-oxidation. This effect of acceleration of the photo-oxidation kinetics by addition of a cationic surfactant was an unexpected result and can be great practical utility even in the case of UV only absorbing metal oxide photocatalysts like $TiO_2$.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A method of photo-oxidizing a hydrocarbon compound, comprising the steps of:

dispersing $MoS_2$ nanoclusters in a solvent containing a hydrocarbon compound contaminant to form a stable solution mixture, said hydrocarbon compound selected from the group consisting of an aromatic hydrocarbon and a chlorinated hydrocarbon; and irradiating said mixture to photo-oxidize said hydrocarbon compound.

2. The method of claim 1 wherein the $MoS_2$ nanoclusters have an average diameter less than approximately 10 nanometers.

3. The method of claim 1 wherein the solvent is selected from the group consisting of water and a polar organic solvent.

4. The method of claim 1 wherein the hydrocarbon compound is selected from the group consisting of phenol, pentachlorophenol, chlorinated biphenols, and chloroform.

5. The method of claim 1 wherein irradiating said mixture is performed with visible light.

6. The method of claim 1 wherein irradiating said mixture is performed with light of wavelengths less than approximately 800 nm.

7. The method of claim 1 wherein the $MoS_2$ nanoclusters in a solvent are prepared by the steps comprising:

dissolving a molybdenum halide salt in a first solvent containing a surfactant with an alcohol cosurfactant to form an inverse micellar solution;

adding said inverse micellar solution to a second solution containing a sulfiding agent to form a solution containing $MoS_2$ nanoclusters;

extracting said $MoS_2$ nanoclusters into a polar solvent containing a stabilizing cationic surfactant;

drying said $MoS_2$ nanoclusters to remove the polar solvent; and adding the dried $MoS_2$ nanoclusters to a second solvent to form a solution of $MoS_2$ nanoclusters in said second solvent.

8. The method of claim 7 wherein the molybdenum halide salt is $MoCI_4$.

9. The method of claim 7 wherein the first solvent is selected from the group consisting of alkanes and aromatic hydrocarbons.

10.The method of claim 7 wherein the sulfiding agent is selected from the group consisting of a metal sulfide, ammonium sulfide, and hydrogen sulfide gas.

11. The method of claim 7 wherein the polar solvent is selected from the group consisting of acetonitrile, methanol and tetrahydrofuran.

12. The method of claim 7 wherein the surfactant is selected from the group consisting of tridodecylmethylammonium chloride, tridodecylmethylammonium bromide, didodecyidimethylammonium bromide, didodecyidimethylammonium chloride, tetraoctylammonium bromide, tetraoctylammonium chloride, and tetraoctylammonium iodide.

13. The method of claim 7 wherein the second solvent is water.

* * * * *